(12) United States Patent
Cabrera et al.

(10) Patent No.: US 10,751,058 B2
(45) Date of Patent: Aug. 25, 2020

(54) ADAPTER ASSEMBLIES FOR SURGICAL DEVICES

(71) Applicant: Covidien LP, Mansfield, MA (US)

(72) Inventors: Ramiro Cabrera, Cheshire, CT (US); Jonathan Sapienza, Orange, CT (US); Stephen Paul, East Hartford, CT (US)

(73) Assignee: Covidien LP, Mansfield, MA (US)

( * ) Notice: Subject to any disclaimer, the term of this patent is extended or adjusted under 35 U.S.C. 154(b) by 760 days.

(21) Appl. No.: 15/209,821

(22) Filed: Jul. 14, 2016

(65) Prior Publication Data

US 2017/0027579 A1    Feb. 2, 2017

Related U.S. Application Data

(60) Provisional application No. 62/197,710, filed on Jul. 28, 2015.

(51) Int. Cl.
*A61B 17/115* (2006.01)
*A61B 17/00* (2006.01)
*A61B 17/29* (2006.01)

(52) U.S. Cl.
CPC ... *A61B 17/1155* (2013.01); *A61B 2017/0046* (2013.01); *A61B 2017/00862* (2013.01); *A61B 2017/291* (2013.01); *A61B 2017/2916* (2013.01)

(58) Field of Classification Search
CPC ...... A61B 2017/291; A61B 2017/0046; A61B 2017/00464; Y10T 403/591; Y10T 403/595; Y10T 403/599

(Continued)

(56) References Cited

U.S. PATENT DOCUMENTS 2,777,340 A    1/1957   Hettwer et al.
2,957,353 A   10/1960   Babacz
(Continued)

FOREIGN PATENT DOCUMENTS

CA    2451558 A1    1/2003
CN    1547454 A    11/2004
(Continued)

OTHER PUBLICATIONS

Extended European Search Report corresponding to counterpart International Application No. EP 14 18 4882.0 dated May 12, 2015.

(Continued)

*Primary Examiner* — Thanh K Truong
*Assistant Examiner* — Katie L Gerth
(74) *Attorney, Agent, or Firm* — Carter, DeLuca & Farrell LLP (57) ABSTRACT

An adapter assembly for connecting an end effector to an actuation assembly is provided. The adapter assembly a base defining a plurality of notches spaced at least partially about a circumference of the base, a handle supported on the base and rotatable about a longitudinal axis of the base, and a latch mechanism supported on the handle assembly and selectively engageable with the base. The latch mechanism includes a latch member and a locking member. The latch member is movable between a first position in which the locking member is received within one of the plurality of notches to lock the handle relative to the base, and a second position in which the locking member is spaced from the plurality of notches to unlock the handle relative to the base.

10 Claims, 7 Drawing Sheets

(58) Field of Classification Search
USPC .................................................. 227/179.1
See application file for complete search history.

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,409,866 A * | 10/1983 | McBride | B25G 1/04 |
| | | | 16/429 |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,033,552 A * | 7/1991 | Hu | B25B 21/00 |
| | | | 173/170 |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,464,300 A * | 11/1995 | Crainich | A61B 17/068 |
| | | | 403/322.1 |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,586,830 A * | 12/1996 | Wanek | A47B 23/025 |
| | | | 108/146 |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A * | 7/1997 | Green | A61B 17/07207 |
| | | | 227/175.2 |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,039,126 A * | 3/2000 | Hsieh | B25B 21/00 |
| | | | 173/170 |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,141,049 B2 | 11/2006 | Stern et al. | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |
| 7,225,964 B2 | 6/2007 | Mastri et al. | |
| 7,238,021 B1 | 7/2007 | Johnson | |
| 7,246,734 B2 | 7/2007 | Shelton, IV | |
| 7,252,660 B2 | 8/2007 | Kunz | |
| 7,328,828 B2 | 2/2008 | Ortiz et al. | |
| 7,364,061 B2 | 4/2008 | Swayze et al. | |

(56) References Cited

U.S. PATENT DOCUMENTS

| | | |
|---|---|---|
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,314,916 B2 * | 4/2016 | Tsuchiya ............ A01G 3/053 |
| 10,588,610 B2 * | 3/2020 | Cabrera ............ A61B 17/2909 |
| 2001/0031975 A1 | 10/2001 | Whitman et al. |
| 2002/0049454 A1 | 4/2002 | Whitman et al. |

(56) References Cited

U.S. PATENT DOCUMENTS

| | | |
|---|---|---|
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0006432 A1* | 1/2005 | Racenet ............ A61B 17/07207 227/176.1 |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0025492 A1* | 2/2012 | Grintz ...................... B62B 7/08 280/647 |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0048581 A1 | 2/2014 | Scirica et al. |
| 2014/0110455 A1 | 4/2014 | Ingmanson et al. |
| 2014/0155923 A1* | 6/2014 | Edwards ............ A61B 18/1482 606/170 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1* | 12/2014 | Zergiebel ................ F16H 19/02 74/89.23 |
| 2015/0014392 A1 | 1/2015 | Williams et al. |
| 2015/0048144 A1 | 2/2015 | Whitman |
| 2015/0076205 A1* | 3/2015 | Zergiebel ......... A61B 17/07207 227/175.1 |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |

(56) References Cited

U.S. PATENT DOCUMENTS

| | | | |
|---|---|---|---|
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | | |
|---|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 2815705 A1 | 12/2014 |
| ES | 2333509 A1 | 2/2010 |
| JP | 2005-125075 A | 5/2005 |
| KR | 20120022521 A | 3/2012 |
| WO | 2011/108840 A2 | 9/2011 |
| WO | 2012/040984 A1 | 4/2012 |

OTHER PUBLICATIONS

Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Chinese Office Action dated Apr. 3, 2020, issued in CN Appln. No. 201610601674, 10 pages.

* cited by examiner

ADAPTER ASSEMBLIES FOR SURGICAL DEVICES

CROSS-REFERENCE TO RELATED APPLICATIONS

This application claims the benefit of and priority to U.S. Provisional Patent Application No. 62/197,710 filed Jul. 28, 2015, the entire disclosure of which is incorporated by reference herein.

BACKGROUND

1. Technical Field

The present disclosure relates generally to adapter assemblies for selectively connecting end effectors to the actuation units of powered surgical devices. More specifically, the present disclosure relates to latch mechanisms for rotationally securing rotation handles of the powered surgical devices relative to the actuation assemblies.

2. Background of Related Art

Powered devices for use in surgical procedures typically convert rotational motion from an actuation assembly to linear motion for effectuating one or more functions, e.g., clamping, stapling, cutting. To permit rotational alignment of an end effector attached to the actuation assembly without the operator having to manipulate the actuation assembly in an uncomfortable or awkward position, adapter assemblies have been developed for enabling selective rotation of the end effector relative to the actuation assembly. Such adapter assemblies generally include a base that is fixedly secured to the actuation assembly and a rotation handle to which an end effector is attached for rotating the end effector relative to the base and the actuation assembly. It would be beneficial to provide an adapter assembly with a latch assembly to permit the selective rotation of the rotation handle relative to the base.

SUMMARY

Accordingly, an adapter assembly for operably connecting an end effector to an actuation assembly is provided. The adapter assembly includes a base configured for operable connection to an actuation assembly, a handle supported on the base and rotatable about a longitudinal axis of the base, and a latch mechanism supported on the handle assembly and selectively engageable with the base. The base defines a plurality of notches spaced at least partially about a circumference of the base. The latch mechanism includes a latch member and a locking member extending from the latch member. The latch member is movable between a first position in which the locking member is received within one of the plurality of notches to lock the handle relative to the base, and a second position in which the locking member is spaced from the plurality of notches to unlock the handle relative to the base.

In embodiments, the base further defines a slot extending at least partially about the circumference of the base and interconnected with the plurality of notches. The locking member may be received within the slot when the latch member is in the second position. The plurality of notches may be spaced at regular intervals about the circumference of the base. The latch member may be configured for operable engagement by a user. The latch mechanism may include a biasing member for biasing the latch member in a distal direction. The base may include a slip ring for accommodating electrical cables extending through the base as the handle rotates relative to the base. The plurality of notches may include a first notch and a second notch disposed opposite the first notch. The locking member may be pivotally secured to the latch member.

In embodiments, an adapter assembly in accordance with the present disclosure includes a base configured for operable connection to an actuation assembly, a handle supported on the base and rotatable about a longitudinal axis of the base, and a latch mechanism supported on the handle assembly and selectively engageable with the base and defining a plurality of notches spaced at least partially about a circumference of the base. The latch mechanism includes a latch member and a locking member operably connected to the latch member. The latch member is movable between a first position in which the locking member is received within one of the plurality of notches to lock the handle relative to the base and a second position in which the locking member is spaced from the plurality of notches to unlock the handle relative to the base.

In embodiments, each of the latch member and the locking member include a plurality of teeth and are operably connected by a pinion. The latch member is biased in a radially outward direction by a compression spring. The latch member and the locking member may be connected by a link member. The link member may be biased in a clockwise direction by a torsion spring. Each of the latch member and the locking member may be configured to move radially relative to the base. The latch member and the locking member may move opposite one another. Movement of the latch member from the first position to the second position may be radially inward.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed adapter assembly for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

Figures 1, 2:
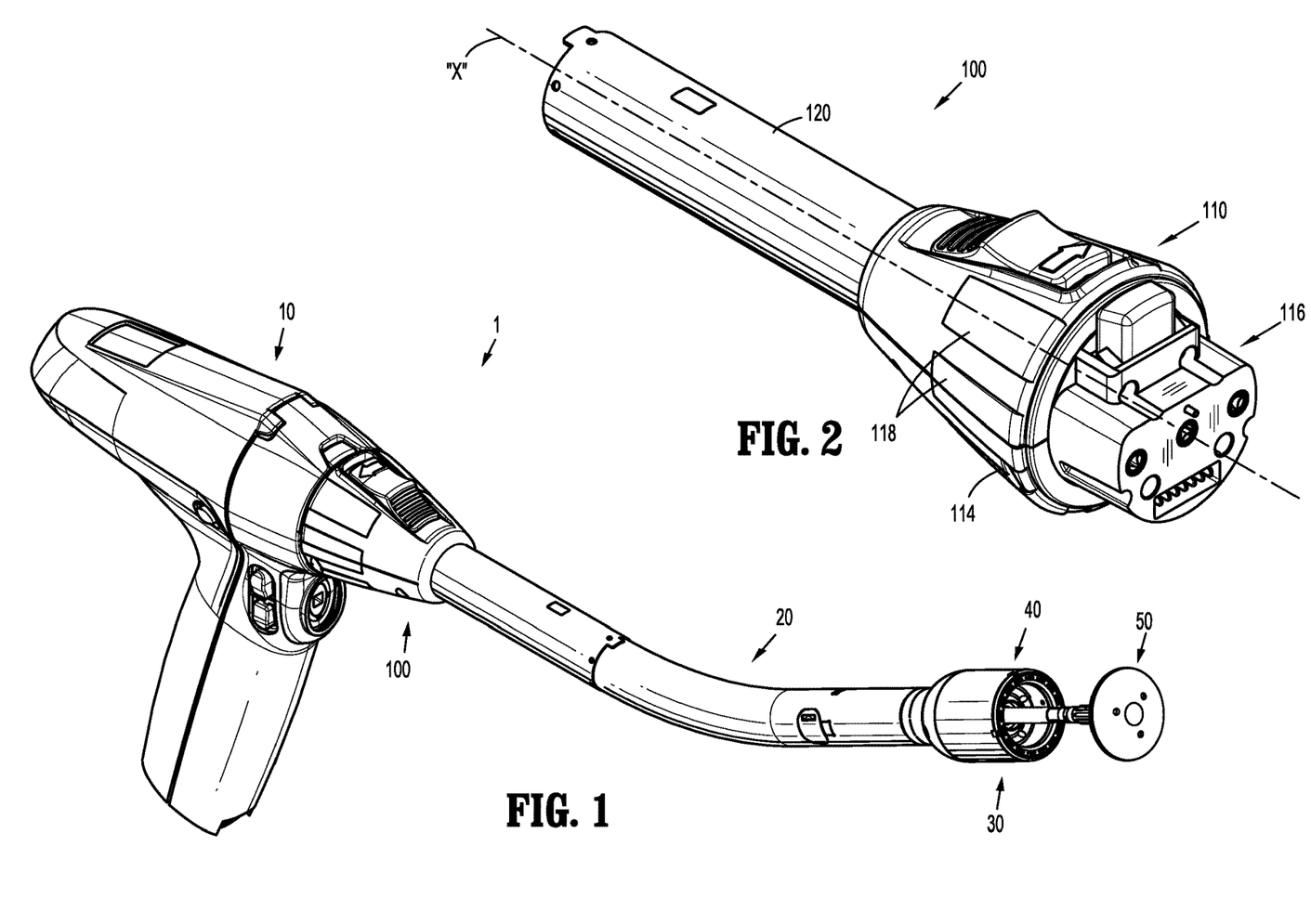
FIG. 1 is a perspective view of an electromechanical surgical device including an adapter assembly, in accordance with an embodiment of the present disclosure, an exemplary actuation assembly, an exemplary extension assembly, and an exemplary end effector.
FIG. 2 is a perspective view of the adapter assembly of FIG. 1.

With reference to FIGS. 1 and 2, an adapter assembly including a latch mechanism in accordance with an embodiment of the present disclosure, shown generally as adapter assembly 100, is a component of a powered handheld electromechanical instrument, shown generally surgical instrument 1. As illustrated in FIG. 1, the surgical instrument 1 includes an actuation assembly 10 configured for selective connection with the adapter assembly 100, and, in turn, the adapter assembly 100 is configured for selective connection with an extension assembly 20. The extension assembly 20 is configured for selective connection with a tool assembly or end effector, e.g. tool assembly 30, which may, in exemplary embodiments, include a loading unit 40 and an anvil assembly 50, for applying a circular array of staples (not shown) to tissue (not shown). For a detailed description of an exemplary actuation assembly, please refer to commonly owned U.S. Pat. Appl. Publ. No. 2012/0253329, the content of which is incorporated by reference herein in its entirety.

Although the latch mechanisms of the present disclosure will be shown and described as relates to the adapter assembly 100, it is envisioned that the presently disclosed latch mechanisms may be adapted for use with adapter assemblies having an alternative configuration and/or the latch mechanisms may be incorporated directly into the actuation assembly. For a detailed description of exemplary adapter assemblies and exemplary extension assemblies, please refer to commonly owned U.S. Provisional Patent Application No. 62/066,518 ("the '518 application"), filed on Oct. 21, 2014, the content of which is incorporated by reference herein in its entirety.

Figure 3:
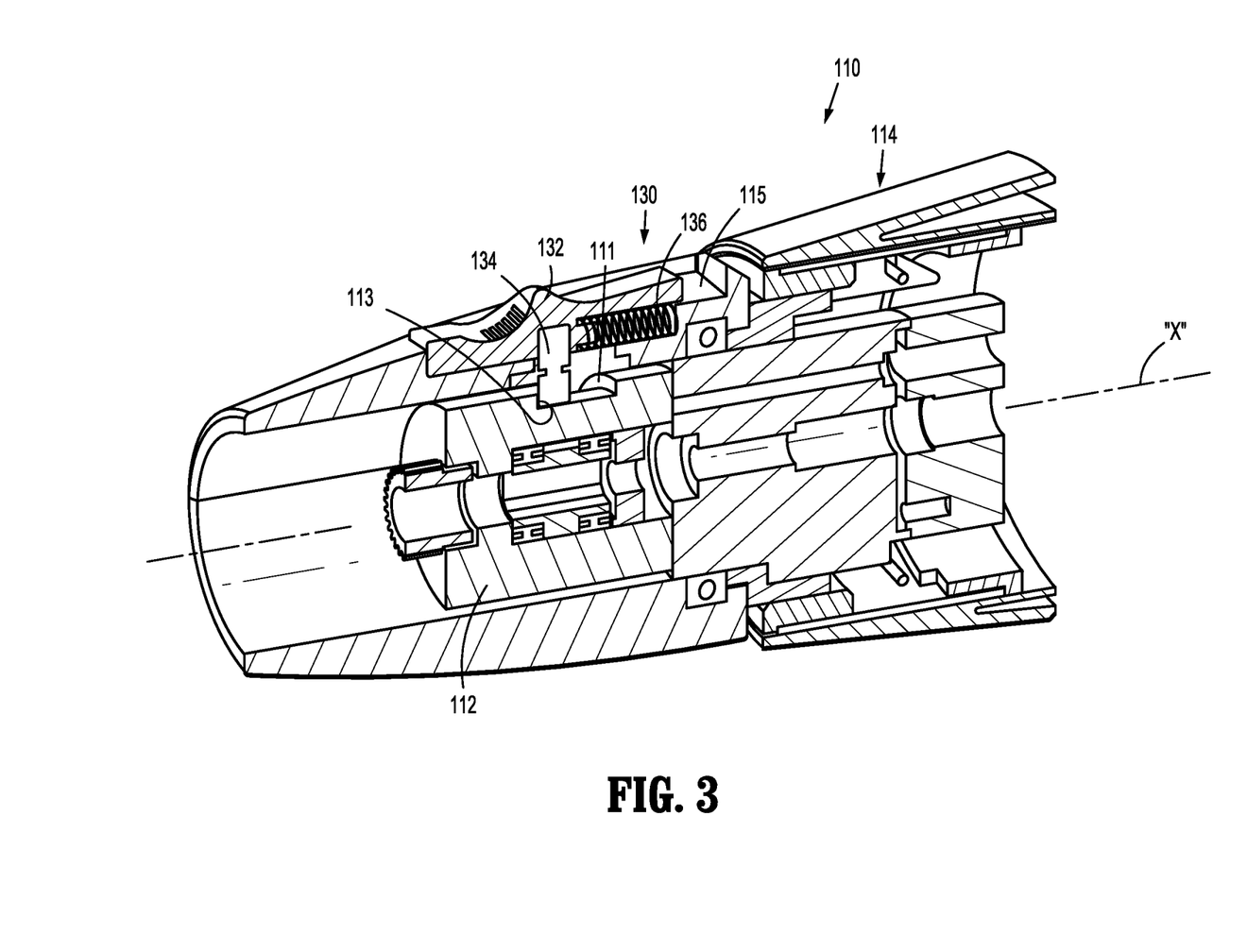
FIG. 3 is a longitudinal cross-sectional perspective side of a handle assembly of the adapter assembly of FIG. 1.

With reference now to FIGS. 2 and 3, the adapter assembly 100 includes a handle assembly 110, and an elongated body portion 120 extending distally from the handle assembly 110. With particular reference to FIG. 3, the handle assembly 110 includes a base or core 112, and a rotation handle 114 rotatably supported about the base 112. The base 112 includes a substantially cylindrical body configured to be selectively secured to the actuation assembly 10 (FIG. 1) by a coupling assembly 116 (FIG. 2). One or more drive assemblies (not shown) extend through the base 112 and the elongated body portion 120 (FIG. 2) of the adapter assembly 100 for transferring power from the actuation assembly 10 (FIG. 1) to the end effector 30 (FIG. 1) for effecting actuation of the end effector 30. For a detailed description of exemplary adapter assemblies, including an exemplary coupling assembly and exemplary drive assemblies, please refer to the '518 application, the content of which was previously incorporated herein.

With continued reference to FIGS. 2 and 3, the rotation handle 114 includes a frustoconical body having a plurality of ridges 118 configured for operable engagement by a user. The elongated body portion 120 (FIG. 2) is fixedly secured to the rotation handle 114 such that rotation of the rotation handle 114 about the longitudinal axis "x" of the adapter assembly 100 causes rotation of the elongate body portion 120 about the longitudinal axis "x". In this manner, an end effector, e.g. tool assembly 30 (FIG. 1), secured to the elongated body portion 120 of the adapter assembly 100, or an end effector secured to an extension assembly, e.g., extension assembly 20 (FIG. 1), which is secured to the elongated body portion 120 of the adapter assembly 100, is rotatable independent of movement of the actuation assembly 10 (FIG. 1) to which the adapter assembly 100 is attached.

With continued reference to FIG. 3, the adapter assembly 100 includes a latch mechanism 130 operably mounted to the rotation handle 114 for securing the rotation handle 114 in a fixed orientation about the longitudinal axis "x" relative to the base 112. The latch mechanism 130 includes a latch member or button 132, a post member 134 extending radially inward from the latch member 132, and a biasing member, i.e., a compression spring 136, operably engaged with the latch member 132.

Figure 4:
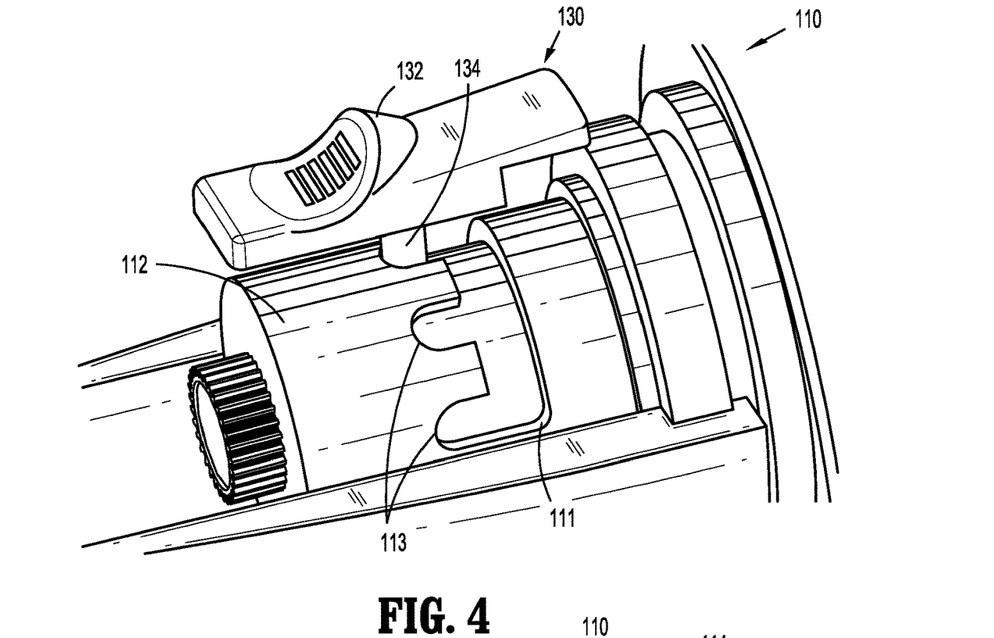
FIG. 4 is a perspective top view of a latch mechanism of the adapter assembly of FIG. 1, shown in a locked position.
Figure 5:
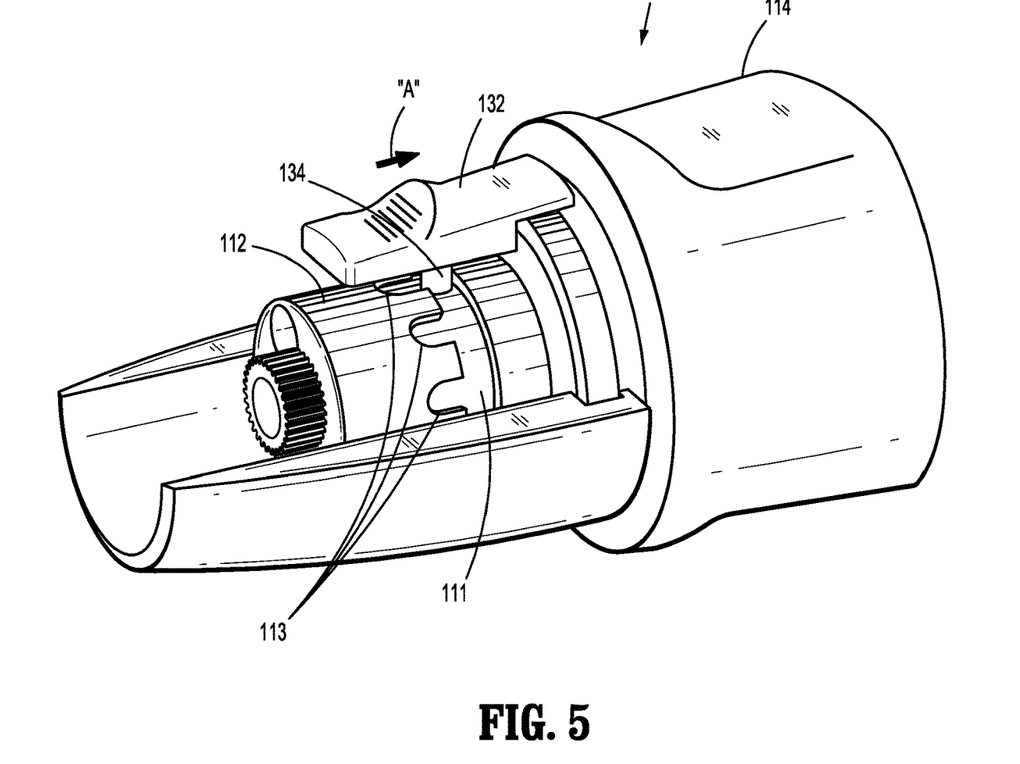
FIG. 5 is a perspective side view of the latch mechanism shown in FIG. 4.

With reference now to FIGS. 3-5, the latch member 132 of the latch mechanism 130 is slidably disposed within a recess 115 (FIG. 3) in the rotation handle 114 and is configured for operable engagement by a user. The latch member 132 is movable between a distal position (FIG. 4) and a proximal position (FIG. 5). The compression spring 136 (FIG. 3) biases the latch member 132 to the distal position. When the latch member 132 is in the distal position, the latch mechanism 130 is in a locked position, i.e., the rotation handle 114 is rotationally secured relative to the base 112. When the latch member 132 is moved in to the proximal position, the latch mechanism 130 is in an unlocked position, i.e., the rotation handle 114 is able to be rotated relative to the base 112.

With continued reference to FIGS. 4 and 5, the base 112 of the handle assembly 110 defines a slot 111 that extends circumferentially about the base 112. As shown, the slot 111 extends approximately eighty degrees (80°) about the base 112 allowing for approximately eighty degrees (80°) degrees of rotation of the rotation handle 114 relative to the base 112. It is envisioned that the slot 111 may extended more or less than eighty degrees (80°), and in embodiments, entirely about the circumference of the base 112. A plurality of notches 113 extend distally from the slot 111. As will be described in further detail below, the notches 113 are configured to selectively receive the post member 134 of the latch mechanism 130 when the latch member 132 is in the distal position. As shown, the notches 111 are equally spaced about the length of the slot 111. In this manner, the rotation handle 114 may be secured at equal intervals of rotation relative to the base 112. It is envisioned that the spacing between the notches 113 may vary. In some embodiments, the base 112 may include only two notches 113, one formed adjacent a first end of the slot 111 and a second notch 113 formed adjacent the second end of the slot 111.

Although shown with the latch mechanism 130 being operable by moving the latch member 132 in the proximal direction to retract the post member 134 from within the notches 113, i.e., to unlock the latch mechanism 130, it is envisioned that for ease of use and/or preference of the user, the latch mechanism 130 may be configured such that the latch member 132 is moved in the distal direction to unlock the latch mechanism 130. Such an arrangement would require the notches 113 in the base 112 to extend distally from the slot 111.

The base 112 of the adapter assembly 100 may define a service groove (not shown) to accommodate electronic cables (not shown), arranged in a coil or a spool, as the rotation handle 114 is rotated relative to the base 112. More particularly, the service groove permits expansion and contraction of the electronic cables during rotation of the rotation handle 114 relative to the base 112.

Figure 6:
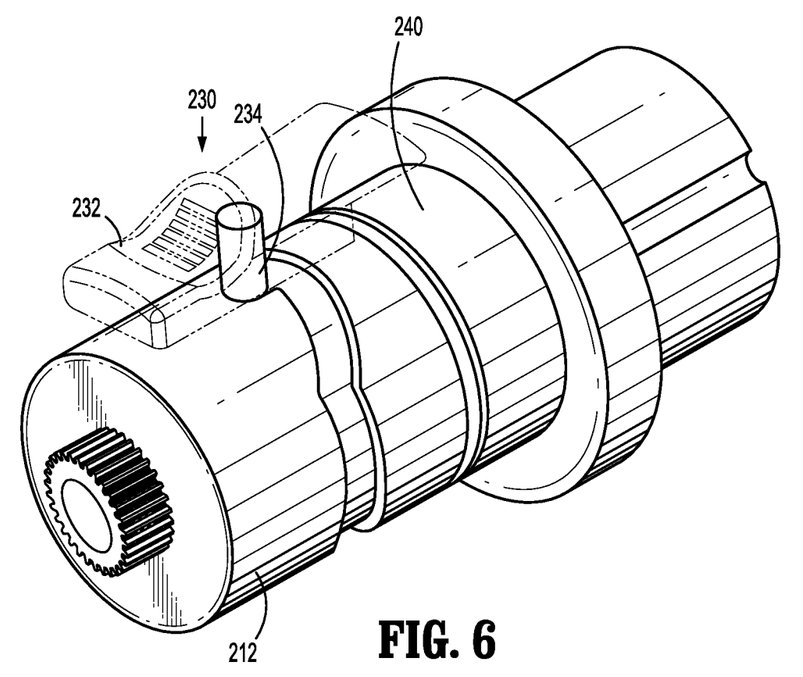
FIG. 6 is a perspective view of a latch mechanism according to an alternative embodiment of the present disclosure, shown in a locked position.
Figure 7:
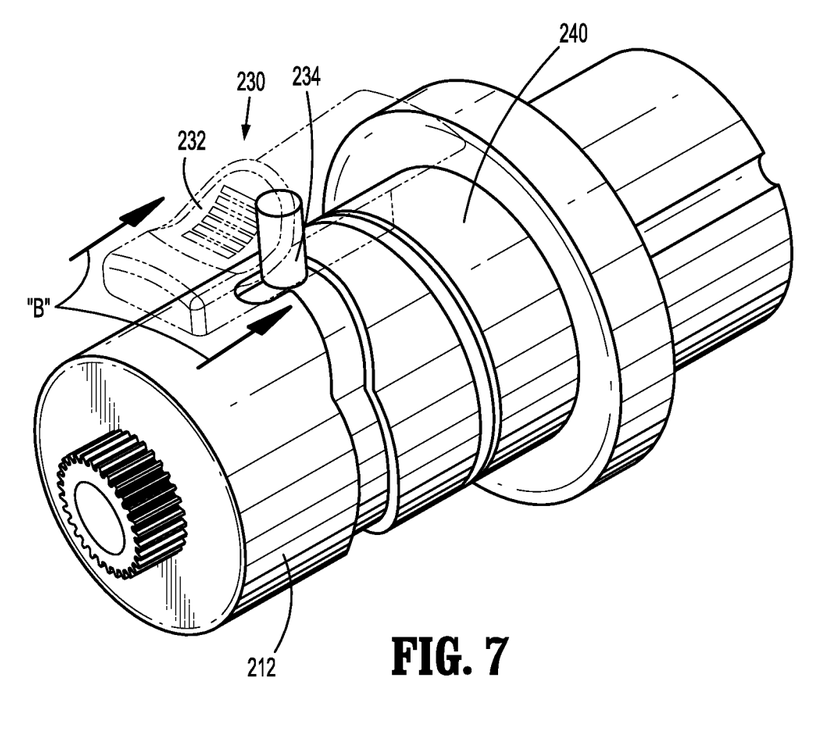
FIG. 7 is a perspective view of the latch mechanism shown in FIG. 6, shown in an unlocked position.

With reference to FIGS. 6 and 7, a latch mechanism according to an alternative embodiment of the present disclosure is shown generally as latch mechanism 230. The latch mechanism 230 is configured such that the rotation handle (not shown) may be rotated, relative to the base 212, approximately one-hundred and eighty degrees (180°). The latch mechanism 230 is substantially similar to latch mechanism 130 described hereinabove and will only be described in detail as relates to the differences therebetween. The latch mechanism 230 is operable with a base 212. The base 212 defines a slot 211 and a first notch 213 and a second notch (not shown).

The latch mechanism 230 includes a latch member 232 and a post member 234 extending radially inward from the latch member 232. As shown in FIG. 6, when the latch member 232 of the latch mechanism 230 is in a distal position, the post member 234 of the latch mechanism 230 is received within the first notch 213 of the base 212, thereby locking the rotation handle (not shown) relative to the base 212. Turning to FIG. 7, proximal movement of the latch member, as indicated by arrows "B", moves the post member 234 from within the first notch 213, thereby unlocking the rotation handle (not shown) and permitting rotation of the rotation handle relative to the base 212. Once the rotation handle has been rotated sufficiently such that a post member 234 of the latch mechanism 230 is no longer aligned with the first notch 213, the latch member 232 may be released. The rotation handle may than continue to be rotated relative to the base 212 until the post member 234 of the latch mechanism 230 is aligned with the second notch (not shown) and a biasing member (not shown) biases the post member 234 within the second notch. An audible and/or tactile indication may be provided to signal to the user that latch mechanism 230 is in a locked position (FIG. 6).

As shown, the base 212 includes a slip ring 240 for accommodating the transmission of electrical power through the base 212 between the actuation assembly 10 (FIG. 1) and the elongated body portion (not shown) extending from the rotation handle (not shown). The slip ring 240 may be any suitable commercially available slip ring. The slip ring 240 enables the one hundred and eighty degrees (180°) rotation of the rotation handle relative to the base 212.

Figure 8:
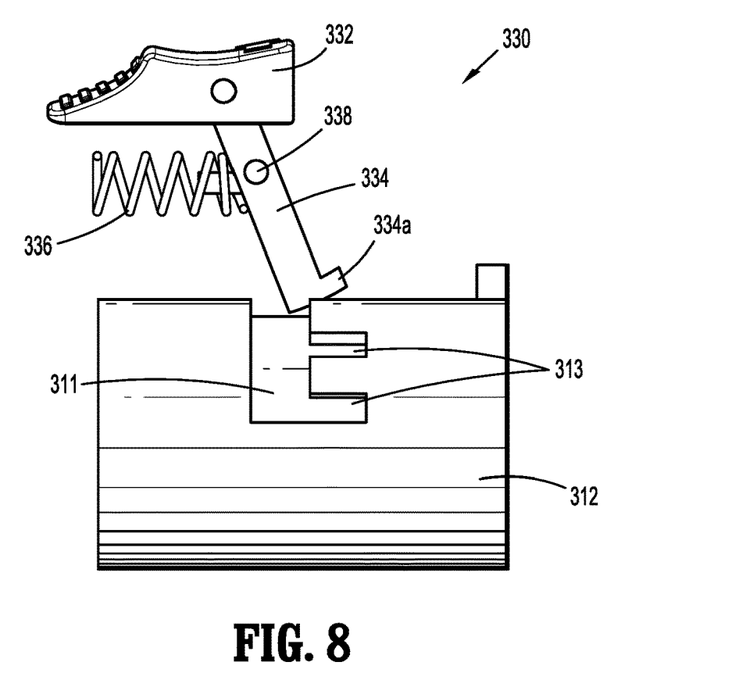
FIG. 8 is side view of a latch mechanism according to another embodiment of the present disclosure, shown in a locked position.
Figure 9:
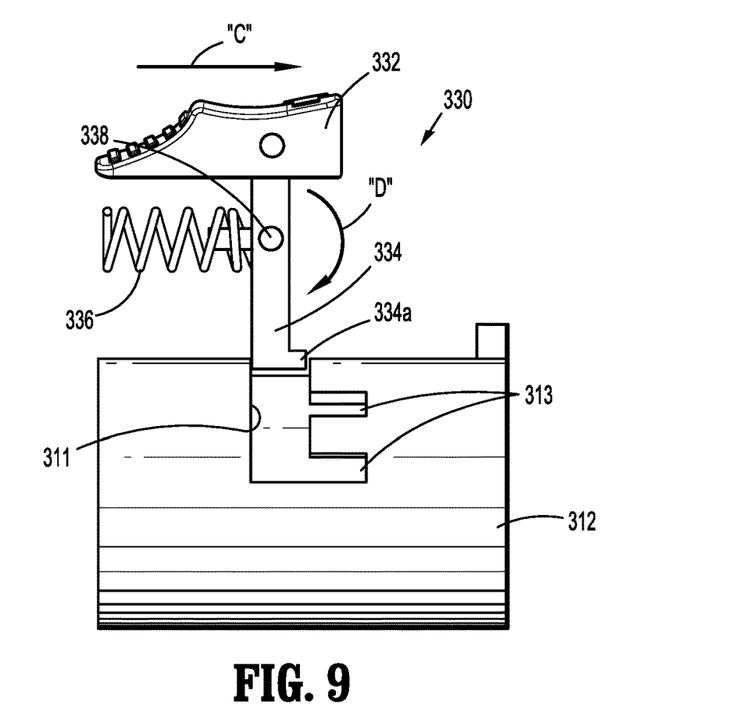
FIG. 9 is a side view of the latch mechanism shown in FIG. 8, shown in an unlocked position.

With reference now to FIGS. 8 and 9, another embodiment of a latch mechanism according to the present disclosure is shown generally as latch mechanism 330. The latch mechanism 330 includes a latch member 332, a post or locking member 334 extending from the latch member 332, and a biasing member, i.e., a compression spring 336, for biasing the latch mechanism 330 to a locked position (FIG. 8).

With continued reference to FIGS. 8 and 9, a base 312 defines a slot 311 extending circumferentially at least partially about the base 312. A plurality of notches 313 are formed in the base 312 extending proximally from the slot 311. The plurality of notches 313 may be equally space about the slot 311. Although not shown, it is envisioned that the slot 311 may extend completely about the circumference of the base 312.

When the latch mechanism 330 is in a locked position (FIG. 8), an end 334a of the locking member 334 of the latch mechanism 330 opposite the latch member 332 is received within one of the plurality of notches 313 to prevent movement of a rotation handle (not shown) relative to the base 312. Proximal movement of the latch member 332, as indicated by arrow "C" in FIG. 9, causes the locking member 334 to pivot about a pivot member 338 thereby moving the end 334a of the locking member 334 from within the notch 313 and into alignment with the slot 311. In this manner, the latch mechanism 330 is moved to the unlocked position (FIG. 9) and the rotation handle (not shown) may be rotated relative to the base 312. Release of the latch member 332 permits the latch mechanism 330 to return to the locked position (FIG. 8), thereby securing the rotation handle relative to the base 312.

Although shown with the latch mechanism 330 being operable by moving the latch member 332 in the proximal direction to unlock the latch mechanism 330, it is envisioned that for ease of use and/or preference of the user, the latch mechanism 330 may be configured such that the latch member 332 is moved in the distal direction to unlock the latch mechanism 330. Such an arrangement would require the plurality of notches 313 in the base 312 to extend distally from the slot 311.

Figure 10:
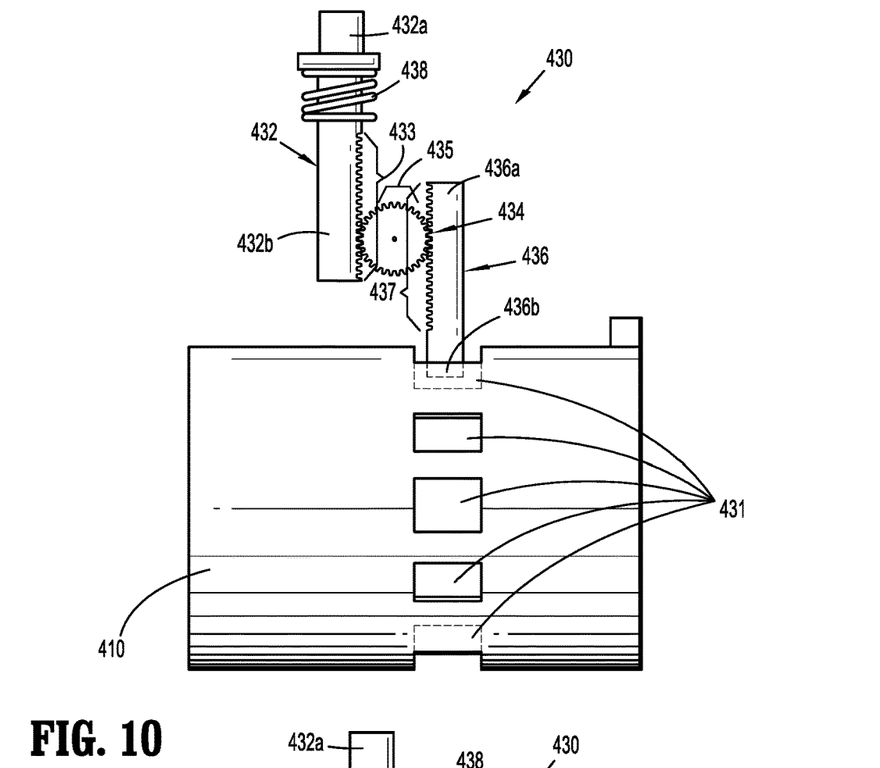
FIG. 10 is side view of a latch mechanism according to still another embodiment of the present disclosure, shown in a locked position.
Figure 11:
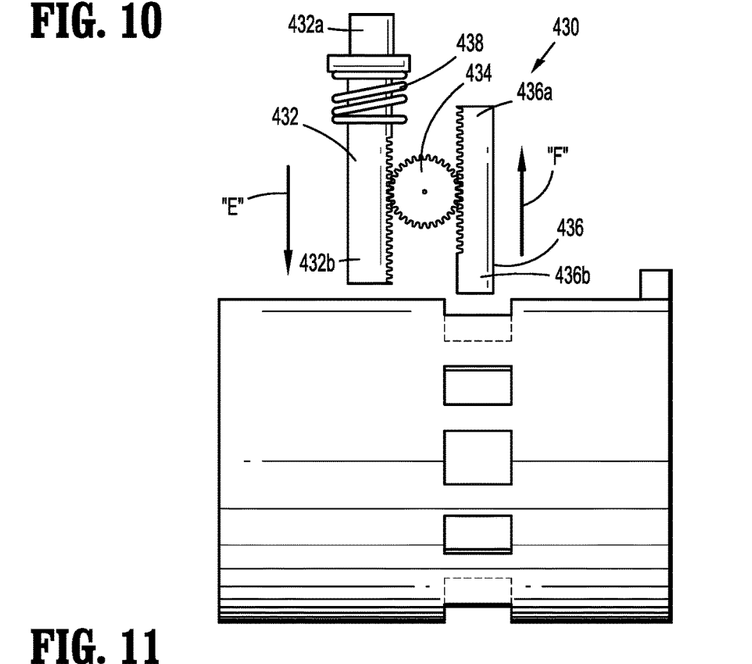
FIG. 11 is a side view of the latch mechanism shown in FIG. 10, shown in an unlocked position.

With reference now to FIGS. 10 and 11, another embodiment of a latch mechanism according to the present disclosure is shown generally as latch mechanism 430. The latch mechanism 430 includes a latch member 432, a pinion 434, and a rack or locking member 436. A biasing member, e.g., compression spring 438, is received about the latch member 432 to bias the latch member 432 radially outward.

The latch member 432 of the latch mechanism 430 includes a first portion 432a configured for operable engagement by a user and a second portion 432b having a plurality of teeth 433. The pinion 434 includes a plurality of teeth 435 formed about a circumference of the pinion 434. The rack member 436 includes a first portion 436a having a plurality of teeth 437 and a second portion 436b configured for operable engagement with a base 410. Each of the latch member 432 and the rack member 436 move radially relative to the base 410.

With continued reference to FIGS. 10 and 11, the plurality of teeth 433 of the latch member 432 operably engage the plurality of teeth 435 of the pinion 434. Similarly, the plurality of teeth 437 of the rack member 436 operably engage the plurality of teeth 435 of the pinion 434. In this manner, and as indicated by arrows "E" and "F" shown in FIG. 11, the latch member 432 and the rack member 436 move in opposite directions. More particularly, when the latch member 432 is depressed, i.e., moves radially inward or towards the base 410, the rack member 436 disengages the base 410, i.e., moves radially outward or away from the base 410.

The base 410 defines a plurality of notches 413 spaced about at least a portion of the circumference of the base 410. The plurality of notches 413 may be spaced at equal or unequal intervals. The plurality of notches 413 are positioned to receive the second portion 436b of the rack member 436 when the latch mechanism 430 is in a locked position (FIG. 10). The base 410 may define a slot (not shown) extending about the circumference of the base 410 interconnecting the plurality of notches 413 to limit the distance the rack member 436 is required to be moved radially to disengage the rack member 436 from the base 410, i.e., to unlock the latch mechanism 430, to permit rotation of the rotation handle (not shown) relative to the base 410.

With reference now to FIG. 10, when the latch mechanism 430 is in the locked position, the second portion 436b of the rack member 436 is received within one of the plurality of notches 413 of the base 410. The bias of the compression spring 438 against the latch member 432 maintains the latch member 432 in a radially outward position which, through operation of the pinion 434, maintains the rack member 436 in a radially inward position. In this manner, the handle assembly (not shown), including the latch mechanism 430, is rotationally locked relative to the base 410.

Turning to FIG. 11, when the latch member 432 of the latch mechanism 430 is depressed, i.e., moved to a radially inward position, as indicated by arrow "E", operation of the pinion 434 moves the rack member 436 radially outward, as indicated by arrow "F", to retract the second portion 436b of the rack member 436 from within one of the plurality of notches 413. Once the second portion 436b of the rack member 436 is disengaged from the base 410, the rotation handle (not shown) is rotatable relative to the base 410.

Release of the latch member 432 of the latch mechanism 430 causes the rack member 436 to return to the radially inward position (due to the biasing forces of the compression spring 438), thereby locking the latch mechanism 430. The latch mechanism 430 may include an audible and/or tactile indicator for indicating to the user that that latch mechanism 430 is in the locked position (FIG. 10). The audible and/or tactile indicator may instead or also indicate to the user that the latch mechanism 430 is in the unlocked position (FIG. 11).

Figure 12:
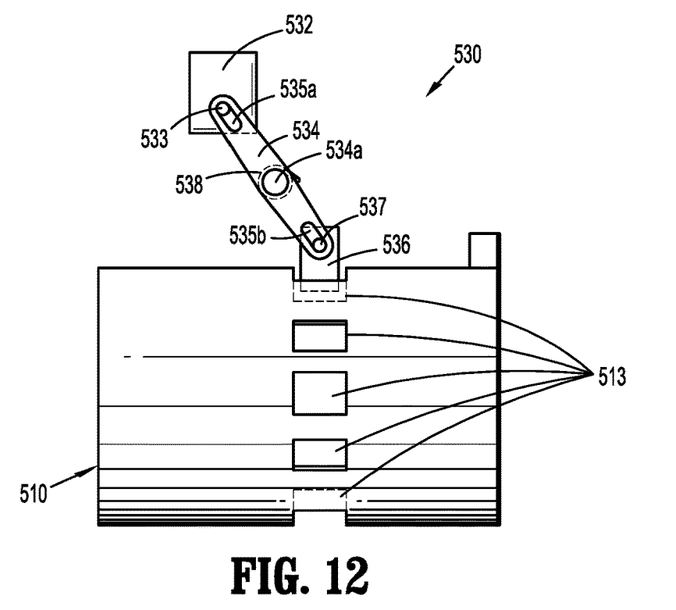
FIG. 12 is side view of a latch mechanism according to yet another embodiment of the present disclosure, shown in a locked position.
Figure 13:
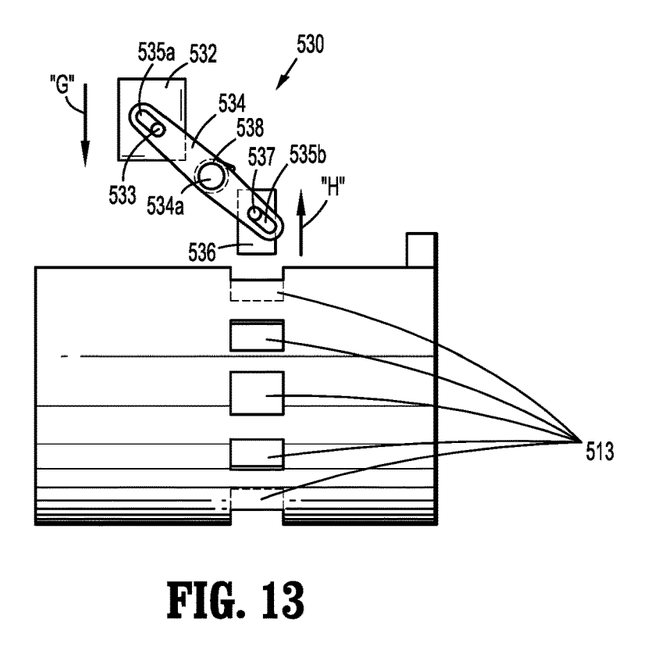
FIG. 13 is a side view of the latch mechanism shown in FIG. 12, shown in an unlocked position.

With reference now to FIGS. 12 and 13, yet another embodiment of a latch mechanism according to the present disclosure is shown generally as latch mechanism 530. The latch mechanism 530 includes a latch member 532, a link member 534, and a locking member 536. A biasing member, e.g., torsion spring 538, is engaged with the link member 534 to bias the link member 534 in a clockwise direction, as shown, to maintain the latch mechanism 530 in a locked position (FIG. 12).

The latch member 532 of the latch mechanism 530 is configured for operable engagement by a user and includes a pin 533 extending outwardly therefrom for engagement with the link member 534. The link member 534 is pivotal about a pivot pin 534a and defines first and second slots 535a, 535b. The locking member 536 includes a pin 537 extending outwardly therefrom for engagement with the link member 534. The locking member 536 is configured for operable engagement with a base 510. Each of the latch member 532 and the locking member 536 move radially relative to the base 510.

With continued reference to FIGS. 12 and 13, the pin 533 of the latch member 532 is received with the first slot 535a of the link member 534 and the pin 537 of the locking member 536 is received within the second slot 535b of the link member 534. The engagement of the latch member 532 and the locking member 536 with the link member 534 is such that the latch member 532 and the locking member 536 move in opposite directions, as indicated by arrows "G" and "H" shown in FIG. 13. More particularly, when the latch member 532 is depressed, i.e., moves radially inward or towards the base 510, the locking member 536 disengages the base 510, i.e., moves radially outward or away from the base 510.

The base 510 defines a plurality of notches 513 spaced about at least a portion of the circumference of the base 510. The plurality of notches 513 may be spaced at equal or unequal intervals and are positioned to receive the locking member 536 when the latch mechanism 530 is in the locked position (FIG. 12). The base 510 may define a slot (not shown) extending about the circumference of the base 510 interconnecting the plurality of notches 513 to limit the distance the locking member 536 is required to move radially to disengage the locking member 536 from the base 510, i.e., to unlock the latch mechanism 530, to permit rotation of the rotation handle (not shown) relative to the base 510.

With particular reference now to FIG. 12, when the latch mechanism 530 is in the locked position, the locking member 536 is received within one of the plurality of notches 513 of the base 510. The bias of the torsion spring 538 on the link member 534 maintains the latch member 532 in a radially outward position and the locking member 536 in a radially inward position. In this manner, the base 510 is rotationally locked relative to the handle assembly (not shown).

Turning to FIG. 13, when the latch member 532 of the latch mechanism 530 is depressed, i.e., moved to a radially inward position, as indicated by arrow "G", operation of the link member 534 moves the locking member 536 radially outward, as indicated by arrow "H", to retract the locking member 536 from within one of the plurality of notches 513. Once the locking member 536 is disengaged from the base 510, the rotation handle (not shown) is rotatable relative to the base 510.

Release of the latch member 532 of the latch mechanism 530 causes the locking member 536 to return to the radially inward position (due to the biasing force of the torsion spring 538), thereby locking the latch mechanism 530. The latch mechanism 530 may include an audible and/or tactile indicator for indicating to the user that that latch mechanism 530 is in the locked position (FIG. 12). The audible and/or tactile indicator may also or instead indicate to the user that the latch mechanism 530 is in the unlocked position (FIG. 13).

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to an actuation assembly, the adapter assembly comprising:
   a base configured for operable connection to the actuation assembly and defining a plurality of notches spaced at least partially about a circumference of the base;
   a handle assembly supported on the base and rotatable about a longitudinal axis of the base; and a latch mechanism supported on the handle assembly and selectively engageable with the base, the latch mechanism including a latch member and a locking member extending from the latch member, wherein the latch member is slidable parallel to the longitudinal axis of the base between a first position in which the locking member is received within one of the plurality of notches to lock the handle relative to the base and a second position in which the locking member is spaced from the plurality of notches to unlock the handle relative to the base.

2. The adapter assembly of claim 1, wherein the base further defines a slot extending at least partially about the circumference of the base and interconnected with the plurality of notches.

3. The adapter assembly of claim 2, wherein the locking member is received within the slot when the latch member is in the second position.

4. The adapter assembly of claim 1, wherein the plurality of notches are spaced at regular intervals about the circumference of the base.

5. The adapter assembly of claim 1, wherein the latch member is positioned to be engaged by a thumb of a user when the user is grasping the handle assembly.

6. The adapter assembly of claim 1, wherein the latch mechanism includes a biasing member for biasing the latch member in a distal direction.

7. The adapter assembly of claim 1, wherein the base includes a slip ring for accommodating electrical cables extending through the base as the handle rotates relative to the base.

8. The adapter assembly of claim 1, wherein the plurality of notches includes a first notch and a second notch disposed one-hundred eighty degrees (180°) opposite the first notch.

9. The adapter assembly of claim 1, wherein the locking member is pivotally secured to the latch member.

10. An adapter assembly for operably connecting an end effector to an actuation assembly, the adapter assembly comprising:
a base configured for operable connection to the actuation assembly and defining a plurality of notches spaced at least partially about a circumference of the base;
a handle assembly supported on the base and rotatable about a longitudinal axis of the base; and
a latch mechanism supported on the handle assembly and selectively engageable with the base, the latch mechanism including a latch member and a locking member operably connected to the latch member, wherein the latch member is slidable parallel to the longitudinal axis of the base between a first position in which the locking member is received within one of the plurality of notches to lock the handle relative to the base and a second position in which the locking member is spaced from the plurality of notches to unlock the handle relative to the base.

* * * * *